(12) United States Patent
Murray et al.

(10) Patent No.: US 11,406,793 B2
(45) Date of Patent: Aug. 9, 2022

(54) INTRODUCTION TO SELF-CATHETERIZATION KIT

(71) Applicant: Hollister Incorporated, Libertyville, IL (US)

(72) Inventors: Michael G. Murray, Ballina (IE); Mark Dillon, Dublin (IE); Patrick E. O'Dowd, Dunsany (IE)

(73) Assignee: Hollister Incorporated, Libertyville, IL (US)

( * ) Notice: Subject to any disclaimer, the term of this patent is extended or adjusted under 35 U.S.C. 154(b) by 668 days.

(21) Appl. No.: 16/335,571

(22) PCT Filed: Sep. 22, 2017

(86) PCT No.: PCT/US2017/052865
§ 371 (c)(1),
(2) Date: Mar. 21, 2019

(87) PCT Pub. No.: WO2018/057835
PCT Pub. Date: Mar. 29, 2018

(65) Prior Publication Data
US 2020/0016366 A1    Jan. 16, 2020

Related U.S. Application Data

(60) Provisional application No. 62/398,711, filed on Sep. 23, 2016.

(51) Int. Cl.
*A61M 25/00* (2006.01)
*A61B 1/00* (2006.01)
*A61M 25/01* (2006.01)

(52) U.S. Cl.
CPC ....... *A61M 25/002* (2013.01); *A61B 1/00144* (2013.01); *A61M 25/0017* (2013.01); *A61M 25/0133* (2013.01); *A61M 2210/1078* (2013.01)

(58) Field of Classification Search
CPC ...... A61B 1/00144; A61M 2210/1078; A61M 25/0017; A61M 25/002; A61M 25/0113; B65D 5/38; B65D 83/0463; B65D 2203/00
See application file for complete search history.

(56) References Cited

U.S. PATENT DOCUMENTS

| | | | |
|---|---|---|---|
| 752,463 A | 2/1904 | Morris | |
| 2,874,707 A * | 2/1959 | Koppel | A45D 29/20 132/315 |
| 3,347,358 A * | 10/1967 | Meyers | A61J 7/0076 206/232 |
| 3,981,398 A * | 9/1976 | Boshoff | A61F 17/00 206/570 |
| 5,836,451 A * | 11/1998 | Dixon | B65D 5/38 206/569 |

(Continued)

FOREIGN PATENT DOCUMENTS

WO    WO 1998036789    8/1998

OTHER PUBLICATIONS

International Search Report and Written Opinion dated Dec. 7, 2017 for International Application No. PCT/US2017/052865.

*Primary Examiner* — Adam Marcetich
(74) *Attorney, Agent, or Firm* — Cook Alex Ltd.

(57) ABSTRACT

A catheter packing assembly that provides directions to the user on the proper procedure for contamination-free use of the catheter.

12 Claims, 4 Drawing Sheets

(56) References Cited

U.S. PATENT DOCUMENTS

| | | | |
|---|---|---|---|
| 5,895,374 A | 4/1999 | Rodsten | |
| 5,941,241 A * | 8/1999 | Weinstein | A61J 1/00 128/200.23 |
| 6,068,115 A | 5/2000 | Boulton | |
| 6,273,260 B1 * | 8/2001 | ColDepietro | A61J 1/035 206/459.5 |
| 6,669,236 B1 | 12/2003 | Hoellwarth-Oberholz | |
| 6,840,379 B2 | 1/2005 | Franks-Farah | |
| 6,926,708 B1 | 8/2005 | Franks-Farah | |
| 7,624,869 B2 | 12/2009 | Primer | |
| 8,391,104 B2 | 3/2013 | de la Huerga | |
| 8,448,786 B2 | 5/2013 | Tomes | |
| 9,427,377 B1 * | 8/2016 | Miceli | A61J 7/04 |
| 2002/0104774 A1 * | 8/2002 | Hammond | A61F 17/00 206/570 |
| 2004/0168951 A1 * | 9/2004 | Mackie, Jr. | A61J 1/03 206/534 |
| 2005/0074483 A1 | 4/2005 | Lange | |
| 2005/0109648 A1 | 5/2005 | Kerzman | |
| 2008/0202978 A1 | 8/2008 | Salomon | |
| 2009/0004055 A1 * | 1/2009 | Darrigrand | A61B 10/0045 422/400 |
| 2009/0126743 A1 * | 5/2009 | Wingert | A61B 50/31 128/898 |
| 2010/0078347 A1 * | 4/2010 | Brinker | A61B 50/30 206/438 |
| 2011/0036746 A1 | 2/2011 | Bear | |
| 2011/0232234 A1 * | 9/2011 | Lockwood | A61M 25/00 53/443 |
| 2012/0025511 A1 * | 2/2012 | Evert | B42D 3/12 281/15.1 |
| 2013/0037440 A1 * | 2/2013 | Danchisin | A61K 8/66 206/570 |
| 2014/0069950 A1 * | 3/2014 | Mason | A61J 1/035 221/1 |
| 2015/0014203 A1 * | 1/2015 | Upchurch | B65D 83/0463 206/462 |
| 2015/0297296 A1 * | 10/2015 | Stauder | A61M 5/002 206/370 |
| 2016/0184148 A1 * | 6/2016 | Johnson | A61B 50/30 206/570 |
| 2016/0228676 A1 | 8/2016 | Glithero | |
| 2017/0119487 A1 * | 5/2017 | Binder | B65D 75/527 |
| 2017/0239144 A1 * | 8/2017 | Terhune | A61J 7/0076 |
| 2017/0296283 A1 * | 10/2017 | Turturro | B65D 75/5827 |

* cited by examiner

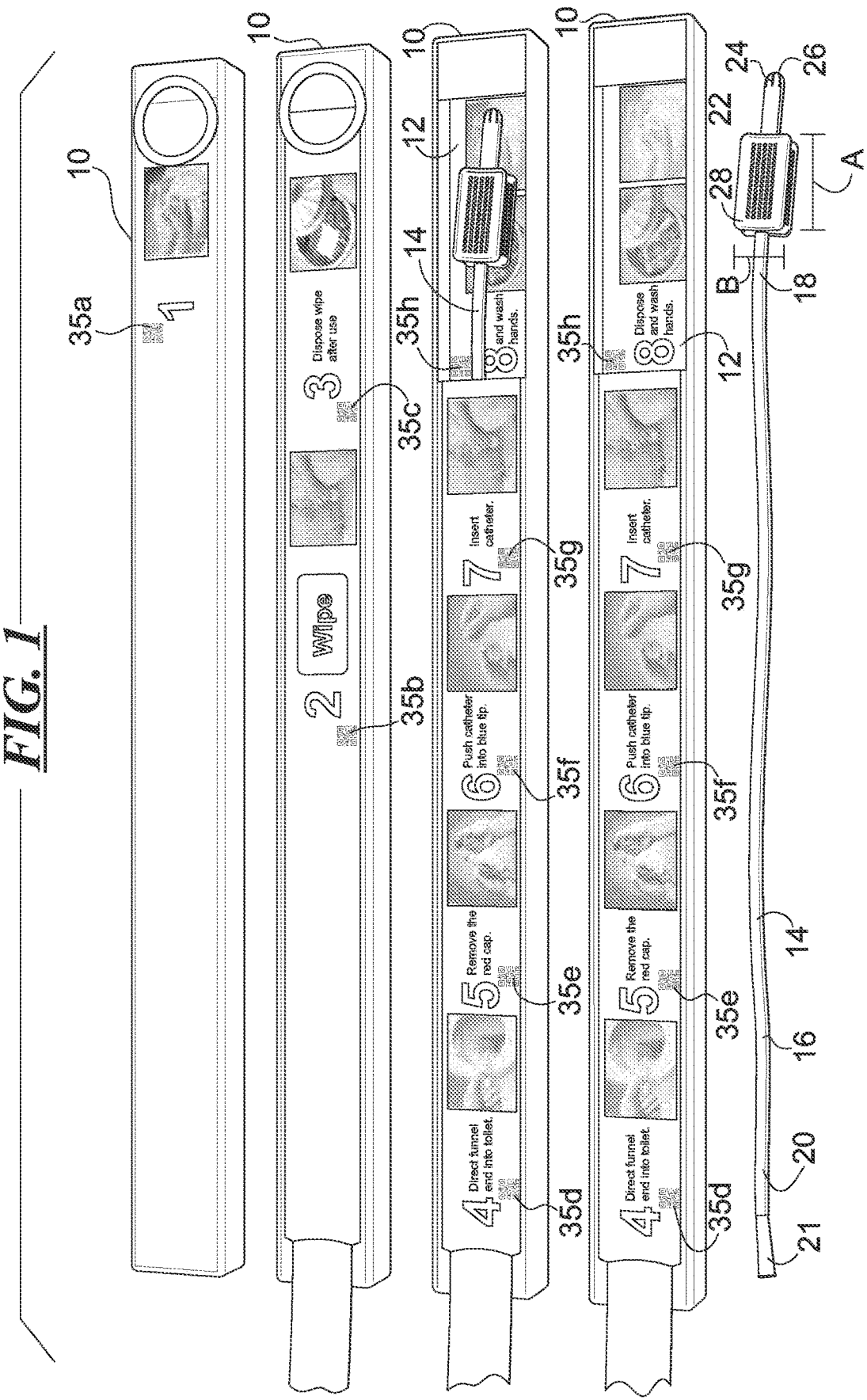

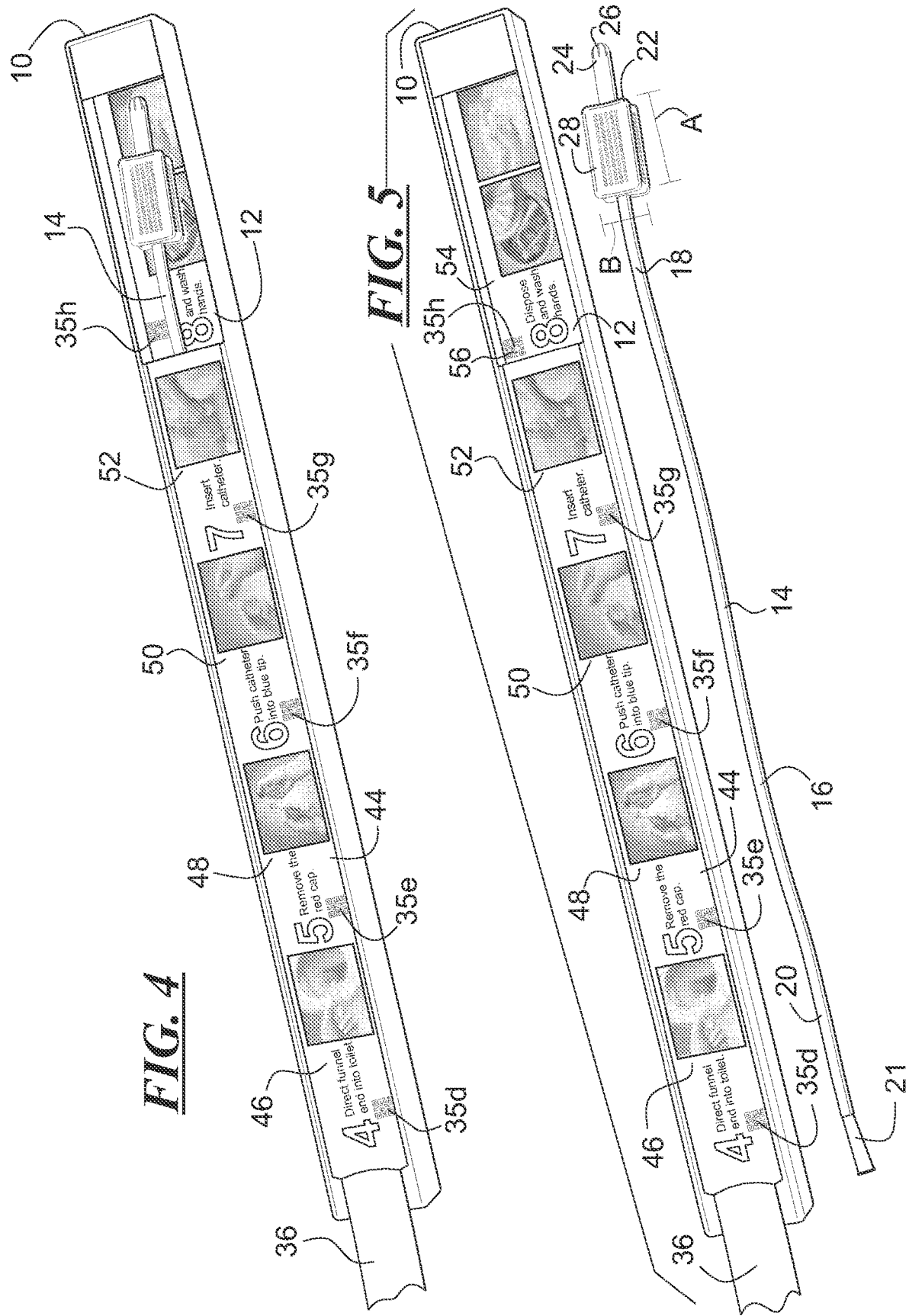

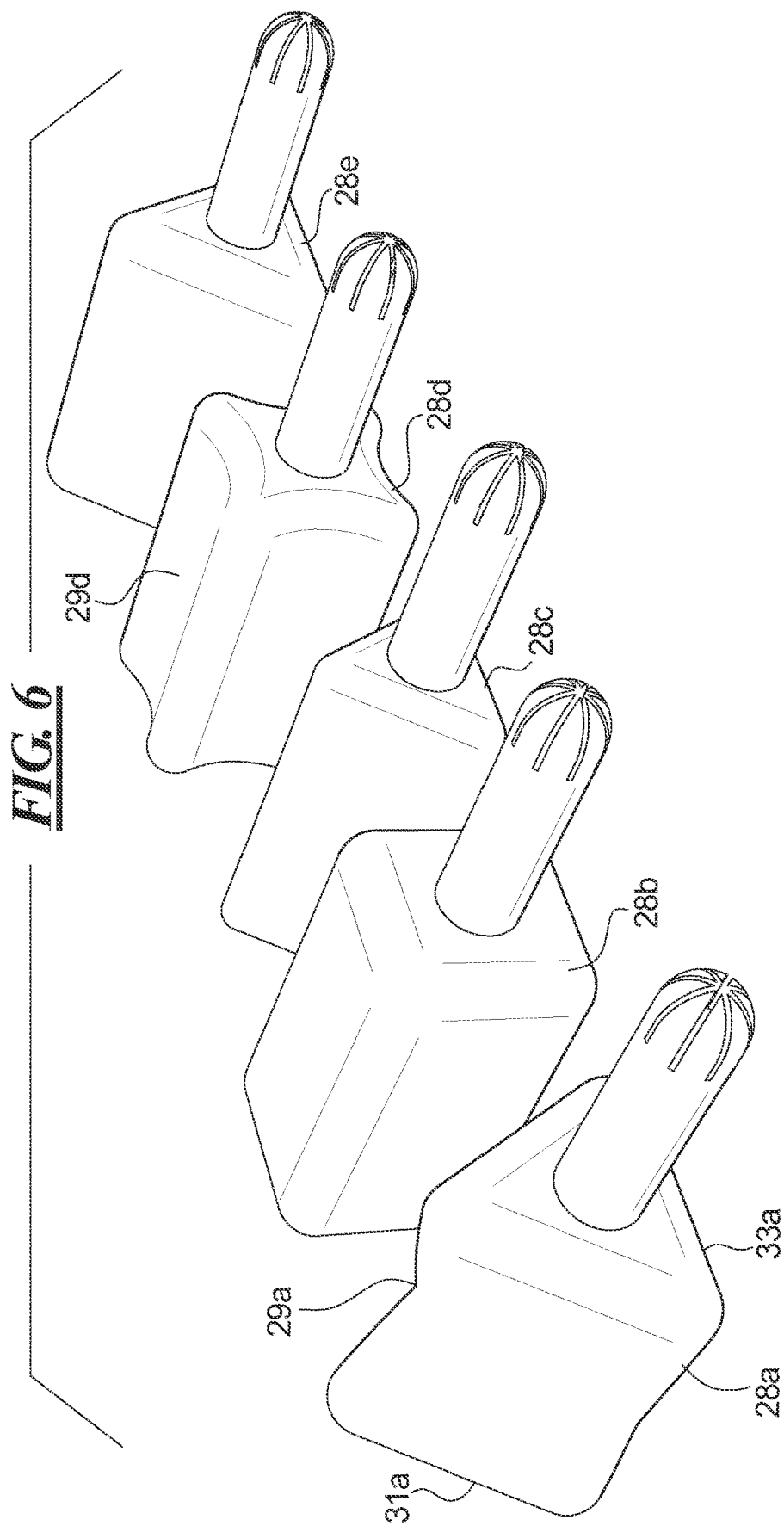

INTRODUCTION TO SELF-CATHETERIZATION KIT

The present application is the U.S. National Stage Application of PCT Application No. PCT/US2017/052865, filed Sep. 22, 2017, which claims the benefit of and priority to U.S. Provisional Patent Application No. 62/398,711, filed Sep. 23, 2016, both of which are incorporated herein by reference.

FIELD OF THE DISCLOSURE

The present disclosure relates generally to packaging for medical devices. More particularly, the present disclosure relates to packaging that instructs a catheter user how to operate the product.

DESCRIPTION OF RELATED ART

Intermittent self-catheterization (ISC) is an intimidating procedure for first-time catheter users. Clinicians usually teach first-time users how to perform the ISC procedure. In fact, a significant amount of time each year is spent training first-time catheter users. Despite having received training, many of these users remain apprehensive about self-catheterizing because they do not feel comfortable performing the procedure alone or did not initially receive proper training. When a person either refuses to catheterize or is improperly trained on the procedure, he is likely to develop a urinary tract infection. Thus, it is imperative that ISC users are both comfortable and adequately trained on the procedure.

Generally, catheter packaging is sold with enclosed instructions.

These instructions are typically written and geared toward the experienced catheter user. While the instructions may generally provide the user with direction, the steps are presented in a manner that may be daunting or confusing to a new user. For example, the directions may instruct a user to "clean the gland" without providing any additional details regarding how the gland should be cleaned. This type of ambiguity may leave a new user hesitant to complete the ISC procedure. For these reasons, there exists a need for a catheter training kit that makes the ISC procedure simple to understand and easier to handle.

SUMMARY

In one aspect of the present disclosure, there is provided a packaging assembly for a self-catheterization that includes a urinary catheter and a package having a plurality of panels including step-by-step written and/or pictorial instructions for use of the urinary catheter. The plurality of panels may be superimposed one atop of the other and sequentially arranged in the order of the step-by-step instructions with a first step being on the top panel and subsequent steps being on lower panels. The panels are moveable relative to succeeding panels to reveal instructions for the subsequent step in the use of the urinary catheter.

In another aspect, a medical packaging assembly includes a medical device and a package having a plurality of panels including step-by-step written and/or pictorial instructions for use of the medical device. The plurality of panels may be superimposed one atop of the other and sequentially arranged in the order of the step-by-step instructions with a first step being on the top panel and subsequent steps being on lower panels. The panels are panels being moveable relative to succeeding panels to reveal instructions for the subsequent step in the use of the medical device.

In yet another aspect, a method of intermittent self-catheterization training includes providing a user with a supply of training catheter packaging assemblies wherein the training catheter packaging assemblies reveal step-by-step instructions as the user opens the packaging assembly.

BRIEF DESCRIPTION OF THE DRAWINGS

FIG. 1 is a top, perspective view of the packaging assembly illustrated in sequential order of the progression of steps involved in catheterization;

FIG. 4 is top perspective view of the packaging assembly of FIG. 1 shown after the second panel has been removed;

FIG. 5 is top perspective view of the packaging assembly shown after the catheter has been removed; and FIG. 6 illustrates catheter training tips that may be used with the packaging assembly described herein.

DETAILED DESCRIPTION OF THE EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

An exemplary packaging assembly 10 for a self-catheterization kit is shown in FIGS. 1-5. FIG. 1 illustrates the packaging assembly 10 at each progressive step in the catheterization process. The packaging assembly 10 reveals the proper or suggested order of contamination-free self-catheterization and may be particularly useful in a training regimen for new catheter users. For example, a healthcare professional may provide initial in-person training to the user regarding the proper or suggested steps for intermittent self-catheterization. The user may then be provided with a supply of training packaging assemblies, such a packaging assembly 10, which the user will use for a suggested or set period of time, e.g., a week to a month. The training packaging assemblies allow the user to become comfortable with performing self-catheterization, i.e., become comfortable with the procedure and the physical steps required to perform contamination-free self-catheterization.

The training packages include step-by-step instructions that are revealed as the user opens the package. Alternatively or in conjunction with the instructions, the training packages may also include one or more machine readable codes that could be read by a machine reader that displays additional content, such as written or oral instructions or an instructional video. For example, the machine readable code could be a bar code or a two dimensions bar code, such as a QR code, and the machine reader could include a camera to capture the code wherein the machine retrieves and displays additional content related to the instructions. In one embodiment, the machine reader could be a portable/mobile device, such as a mobile phone, tablet or computer. In another embodiment, the machine readable code could be wirelessly connected or detectable by the machine reader. For example the machine readable code could be an RFID tag that is wirelessly connected or detectable by the machine reader, which may be any of the above mentioned devices.

Once the user has become comfortable with self-catheterization, the user will discontinue use of the training packaging assembly and graduate to using common everyday self-catheterization packaging assemblies.

Figure 2A:
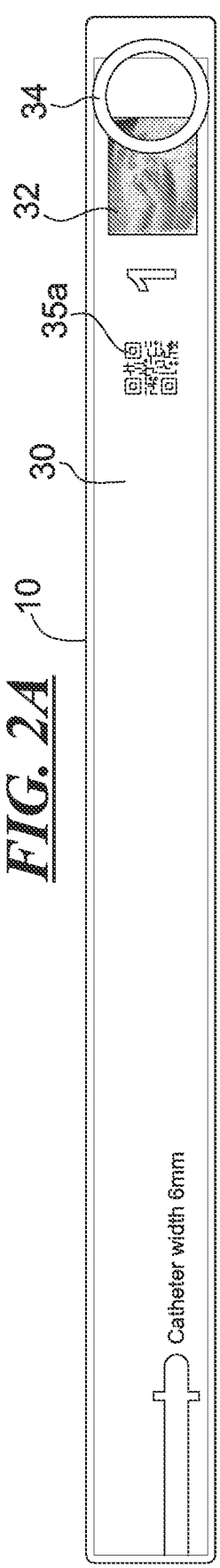
FIG. 2A is a top plan view showing the packaging assembly of FIG. 1.
Figure 2B:
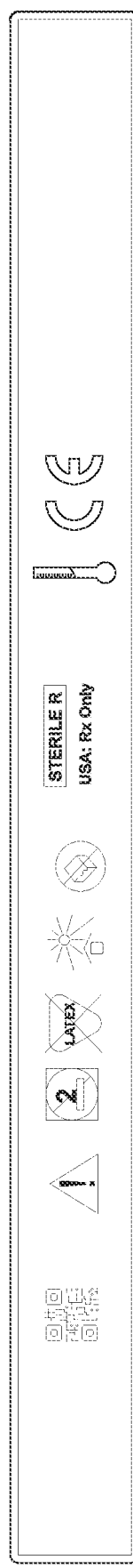
FIG. 2B is a bottom plan view of the packaging assembly of FIG. 1.

Referring to FIGS. 1, 2A and 2B, in the illustrate embodiment, packaging assembly 10 has a box-like configuration that includes a compartment 12 (FIGS. 1 and 4) for containing catheter 14, which may be any suitable urinary catheter. The box-like packaging assembly 10 may be made from paper/cardboard, metal foil, polymer films, metal/polymer multi-layered foils or combinations thereof. In one embodiment, for example, the packaging assembly may take the form of a pliable or flexible package made from metal and/or polymer films.

FIGS. 1 and 5 illustrate an exemplary catheter 14 that includes a catheter shaft 16 having a proximal insertion end 18 and a distal drainage end 20 having a funnel 21 associated therewith. The catheter 14 may, optionally, include an insertion aid 22 associated with the proximal insertion 18 of the catheter shaft 16. The insertion aid 22 includes a passageway in which the catheter 14 is advanced therethrough. The insertion aid 22, optionally, may include an insertion tip 24 that is inserted into the urethral opening prior to advancement of the catheter 14. The insertion tip 24 may, optionally, be covered by a removable cap (not shown). The distal end of the insertion tip 24 includes a normally closed opening 26 through which the catheter 14 is advanced to insert the catheter into the urethra. The insertion aid 22 may be gripped by the user to handle the catheter and insert the insertion tip 24 of the insertion aid 22 into the urethral opening. After the insertion tip 24 is inserted into the urethra, the catheter 14 is then advanced through the insertion aid 22 and the insertion tip 24 into urethra. If the insertion aid 22 does not have an insertion tip, the insertion aid 22 may be used to insert the insertable end 18 of catheter 14 directly into the urethra.

In the embodiment shown, the insertion aid 22 has an oversized gripping portion 28 that may be easier for a newer user to grip. For example, the gripping portion 28 may have a length A of about 20 mm to 45 mm in the direction of the axis of the catheter 14 and a cross-sectional width B of in between about 20 mm or greater. As illustrated in FIG. 6 the oversized gripping portion 28 may have different shapes and sizes, as shown for example by gripping portions 28a, 28b, 28c, 28d and 28e. For example, the gripping portion may have a triangular, rectangular, round or star-shaped cross-section. The gripping portion may also have contoured, curved or indented outer surface(s). For example, gripping portion 28a includes an indent 29a between the proximal and distal ends 31a and 33a of the gripping portion 28a. The indent 29a may circumscribe the gripping portion or may be on one or more sides. Gripping portion 28d includes concaved sides 29d. Also, the gripping portion 28 may be textured. For example, it may include bumps or ridges. The shape and size of the gripping portion 28 may be tailored to the individual users comfort and preference.

FIG. 2A shows top side of the packaging assembly 10 and FIG. 2b shows the bottom side of the packaging assembly. Referring to FIG. 2A, on the top side of the packaging assembly 10 there is a first removable panel 30 which includes the first step 32 of the instructions for use of the catheter. The instructions and associated steps may be in written textual and/or pictorial format and the order of the steps may be indicated by alpha or numeric indicators (i.e., A, B, C or 1, 2, 3). In the illustrated embodiment, the first step 32 of washing the user's hands is shown pictorially and indicated by the numeral "1". The removable panel 30 may optionally include a machine readable code 35a that may be read by a machine reader. The machine readable code 35a, and those discussed below, may be any of the above discussed machine readable codes. In the illustrated embodiment, the machine readable code 35a is a QR code that may be read by an optical machine reader, such as the camera of a mobile phone or tablet. The code may be associated with content obtainable from the internet or stored in the machine reader. When the machine reader reads the machine readable code 35a, the machine reader displays or is connected to a device that displays the associated content, which may be additional written or oral instructions or a video. For example, the user may use his/her mobile phone to read the QR code wherein the mobile phone accesses the associated content and displays such content to the user. The panel 30 also includes a gripping portion, such as a ring 34, which the user may grip and pull to remove or peel back the first panel.

Figure 3:
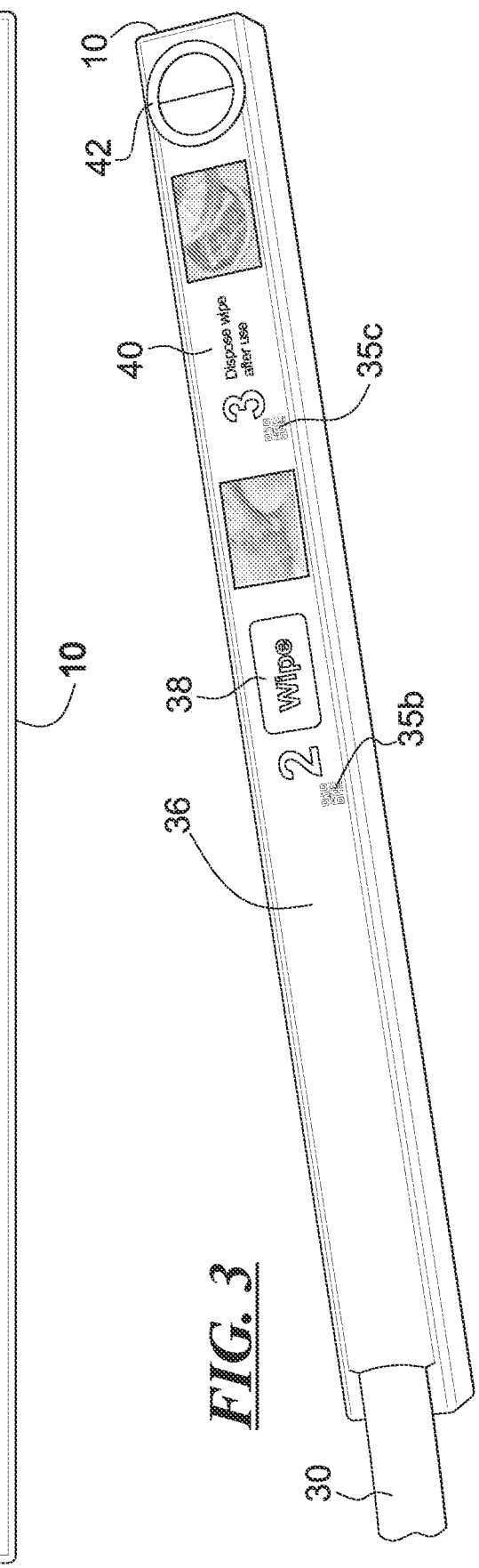
FIG. 3 is a top, perspective view of the packaging assembly of FIG. 1 shown after the first panel has been removed.

FIG. 3 shows the first panel 30, which was superimposed over a second panel 36, removed to expose the second panel 36 to the user. In the illustrated embodiment, the second panel 36 includes the second and third steps 38, 40 for self-catheterization contained thereon. The second panel 36 may optionally include machine readable codes 35b and 35c associated with steps 38 and 40, respectively. The second step 38 of using an antiseptic wipe to clean the gland of the penis is provided pictorially and in text and is indicated by the number "2". The antiseptic wipe may be supplied separately from the packaging assembly 10 or may be attached or contained within the packaging assembly 10. For example, the wipe may be held in a compartment that is integral with the second panel 36 or a package containing the antiseptic wipe may be attached to the second panel 36 or to the outside of the packaging assembly 10. The third step 40 of disposing of the spent antiseptic wipe is also provided pictorially and in text and is indicated by the number "3".

The second panel 36 also includes a gripping portion, such as a ring 42, which the user may grip and pull to remove or peel back the second panel 36. Referring to FIG. 4, when the second panel 36, which is superimposed over the third panel 44, is removed, the third panel 44 is revealed to provide the user with further instructions. Additionally, in the illustrated embodiment, when the second panel 36 is removed, an opening or access to the compartment 12 containing the catheter 14 is exposed so that the use may remove the catheter 14.

In the illustrated embodiment, the third panel 44 includes the fourth, fifth, sixth and seventh steps 46, 48, 50, and 52 for self-catheterization. The third panel 44 may optionally include machine readable codes 35d, 35e, 35f and 35g associated with steps 46, 48, 50, and 52, respectively. The fourth step 46 of removing the catheter 14 from the packaging assembly and directing the funnel 21 of the catheter 14 into the toilet is provided pictorially and in text and is indicated by the number "4". The fifth step 48 of removing the protective cap from the introducer aid 22 is also provided pictorially and in text and is indicated by the number "5". The sixth step of pushing the catheter 14 into the insertion aid 22 is provided pictorially and in text and is indicated by the number "6". The seventh step of inserting the insertion aid 22 and catheter 14 are provided pictorially and in text and are indicated by the number "7".

Referring to FIG. 5, when the catheter 14 is removed from the compartment 12, the eighth step 54 of disposing the catheter 14 and washing hands are exposed. In the illustrated embodiment, the eighth step 54 is provided on a bottom panel 56 defining a portion of compartment 12 that contains the catheter 14. The bottom panel 56 may also include a machine readable code 35*h*, which is associated with step 54.

It will be understood that the package 10 may be used with any suitable urinary catheter and that depending on the catheter and its intended use, the instructions and additional content associate with the machine readable code may vary depending on such use. For example, instructions for use may vary between male catheters and female catheters or between hydrophilic catheters and gel-lubricated catheters.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A self-catheterization intermittent urinary catheter training packaging assembly, comprising:
    an intermittent urinary catheter;
    a package having a compartment containing the intermittent urinary catheter;
    the package comprising a plurality of panels including step-by-step written and/or pictorial self-catheterization training instructions for using the intermittent urinary catheter, the plurality of panels being superimposed one directly atop of the other and sequentially arranged in the order of the step-by-step self-catheterization training instructions;
    wherein a top superimposed panel is removable from a succeeding underlying panel to reveal the step-by-step self-catheterization training instructions of the succeeding underlying panel; and
    wherein one of the underlying panels has an opening therethrough for removing the intermittent catheter from the compartment of the package.

2. The packaging assembly of claim 1, wherein at least one panel of the plurality of panels is removeable relative to a succeeding underlying panel to expose a device that assists in the use of the intermittent urinary catheter.

3. The packaging assembly of claim 2, wherein the device is an infection prevention device.

4. The packaging assembly of claim 2, wherein the device is an antiseptic wipe.

5. The packaging assembly of claim 1, wherein a device associated with a step of self-catheterization is simultaneously presented while revealing the succeeding underlying panel displaying the instructions for the associated step.

6. The packaging assembly of claim 1, wherein at least one panel of the plurality of panels provides instructions for multiple steps.

7. The packaging assembly of claim 1, wherein the package is generally rectangular.

8. The packaging assembly of claim 1, wherein the package has a longitudinal direction and the panels are peelable in the longitudinal direction.

9. The packaging assembly of claim 1, further including one or more machine readable codes associated with the step-by-step self-catheterization training instructions.

10. The packaging assembly of claim 1, further including an insertion aid within the compartment of the package.

11. The packaging assembly of claim 10, wherein the insertion aid has a length in the direction of an axis of the intermittent urinary catheter of about 20 mm to 45 mm and a cross-sectional width of about 20 mm or greater.

12. The packaging assembly of claim 11, wherein the insertion aid includes a gripping portion having a triangular, rectangular, round or star-shaped cross-section.

* * * * *